(12) United States Patent
Triva

(10) Patent No.: US 10,517,575 B2
(45) Date of Patent: Dec. 31, 2019

(54) FLOCKED SWAB AND METHOD FOR COLLECTION AND TRANSFER OF SAMPLES OF BIOLOGICAL MATERIAL

(71) Applicant: Copan Italia S.p.A., Brescia (IT)

(72) Inventor: Daniele Triva, Brescia (IT)

(73) Assignee: Copan Italia S.p.A., Brescia (IT)

( * ) Notice: Subject to any disclaimer, the term of this patent is extended or adjusted under 35 U.S.C. 154(b) by 699 days.

(21) Appl. No.: 14/901,588

(22) PCT Filed: Jun. 13, 2014

(86) PCT No.: PCT/IB2014/062201
§ 371 (c)(1),
(2) Date: Dec. 28, 2015

(87) PCT Pub. No.: WO2014/207598
PCT Pub. Date: Dec. 31, 2014

(65) Prior Publication Data
US 2016/0367227 A1    Dec. 22, 2016

(30) Foreign Application Priority Data
Jun. 28, 2013   (IT) .................................. MI13A1088

(51) Int. Cl.
*A61B 10/00*   (2006.01)
*A61F 13/38*   (2006.01)
(Continued)

(52) U.S. Cl.
CPC .......... *A61B 10/0045* (2013.01); *A61B 10/02* (2013.01); *A61F 13/38* (2013.01);
(Continued)

(58) Field of Classification Search
CPC .............. G01N 2001/028; A61F 13/38; A61B 2010/0216; A61B 10/02
See application file for complete search history.

(56) References Cited

U.S. PATENT DOCUMENTS 4,803,998 A * 2/1989 Kezes ................ A61B 10/0096
435/307.1
5,334,502 A * 8/1994 Sangha .............. A61B 10/0051
422/412
(Continued)

FOREIGN PATENT DOCUMENTS

EP    1608268    11/2007
EP    2263548    12/2010
(Continued)

OTHER PUBLICATIONS

PCT International Search Report and Written Opinion of the International Searching Authority, PCT/IB2014/062201, dated Sep. 23, 2014, 12 pages.

*Primary Examiner* — Patrick Fernandes
(74) *Attorney, Agent, or Firm* — Fish & Richardson P.C.

(57) ABSTRACT

A flocked swab for collection and transfer of samples of biological material, in which the swab comprises a support body having an elongate conformation and having a first end portion and a gripping portion, and a flocked layer defined by a plurality of fibres attached and arranged on the first portion of the support body by flocking, so as to realize a flocked collecting portion aimed at absorbing a quantity of a sample of biological material, the first portion of the support body being provided with a first weakening portion aimed at enabling and facilitating a selective breakage of the swab at the first portion and a separation of a first part of the flocked collecting portion from a second part of the flocked collecting portion and from the gripping portion.

26 Claims, 4 Drawing Sheets

(51) Int. Cl.
*G01N 1/02* (2006.01)
*A61B 10/02* (2006.01)

(52) U.S. Cl.
CPC ........ *G01N 1/02* (2013.01); *A61B 2010/0225* (2013.01); *G01N 2001/028* (2013.01)

(56) References Cited

U.S. PATENT DOCUMENTS

| | | | | |
|---|---|---|---|---|
| 5,623,941 | A * | 4/1997 | Hedberg | A46B 3/02 600/569 |
| 8,696,595 | B2 * | 4/2014 | Sangha | A61B 10/0045 600/562 |
| 2006/0142668 | A1 * | 6/2006 | Triva | A61B 10/0045 600/572 |
| 2008/0077046 | A1 * | 3/2008 | Burg | A61B 10/0291 600/569 |
| 2008/0148872 | A1 * | 6/2008 | Iheme | G01N 35/1079 73/864.11 |
| 2009/0023219 | A1 * | 1/2009 | Perez | A61B 10/0096 436/18 |
| 2010/0124780 | A1 * | 5/2010 | Larkin | A61B 10/0096 435/307.1 |
| 2010/0125223 | A1 * | 5/2010 | Roan | A61B 10/02 600/569 |

FOREIGN PATENT DOCUMENTS

| | | |
|---|---|---|
| EP | 2395337 | 12/2011 |
| WO | WO86/03395 | 6/1986 |
| WO | WO93/11434 | 6/1993 |
| WO | WO2004/086979 | 10/2004 |
| WO | WO2011/095599 | 8/2011 |

\* cited by examiner

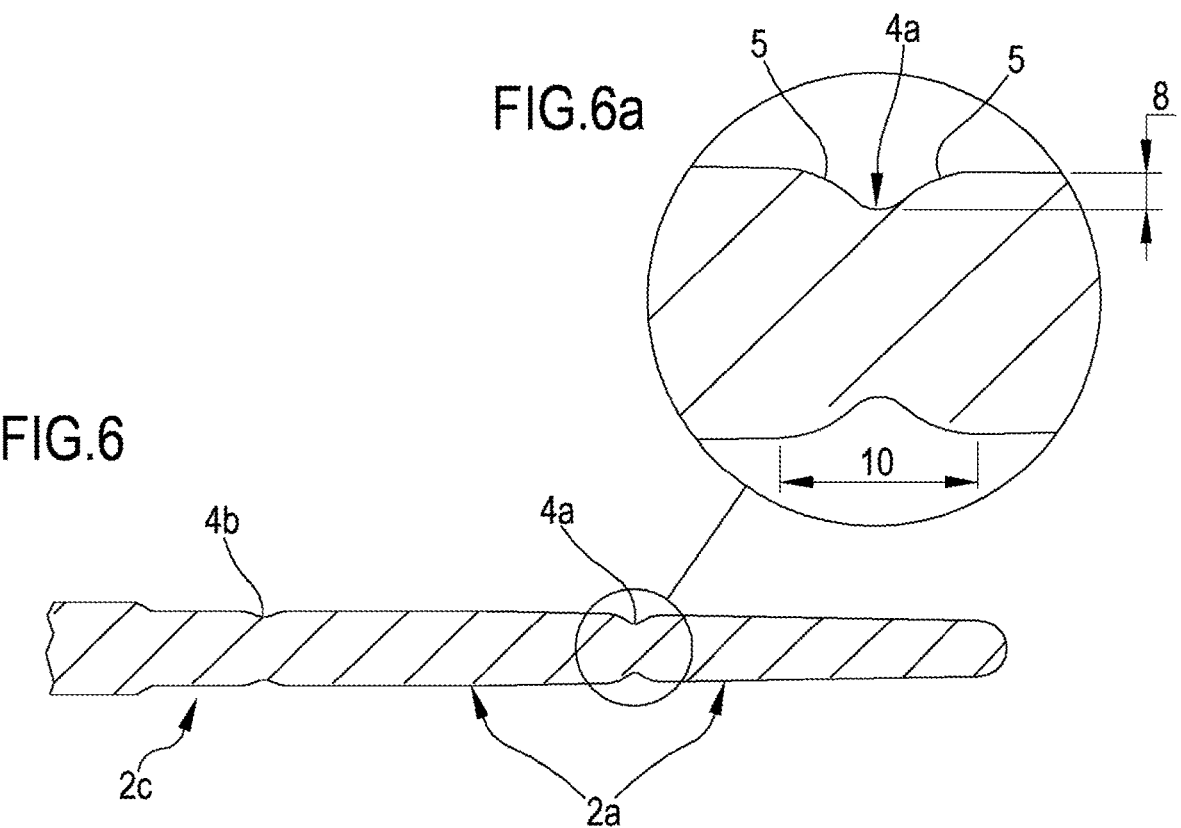
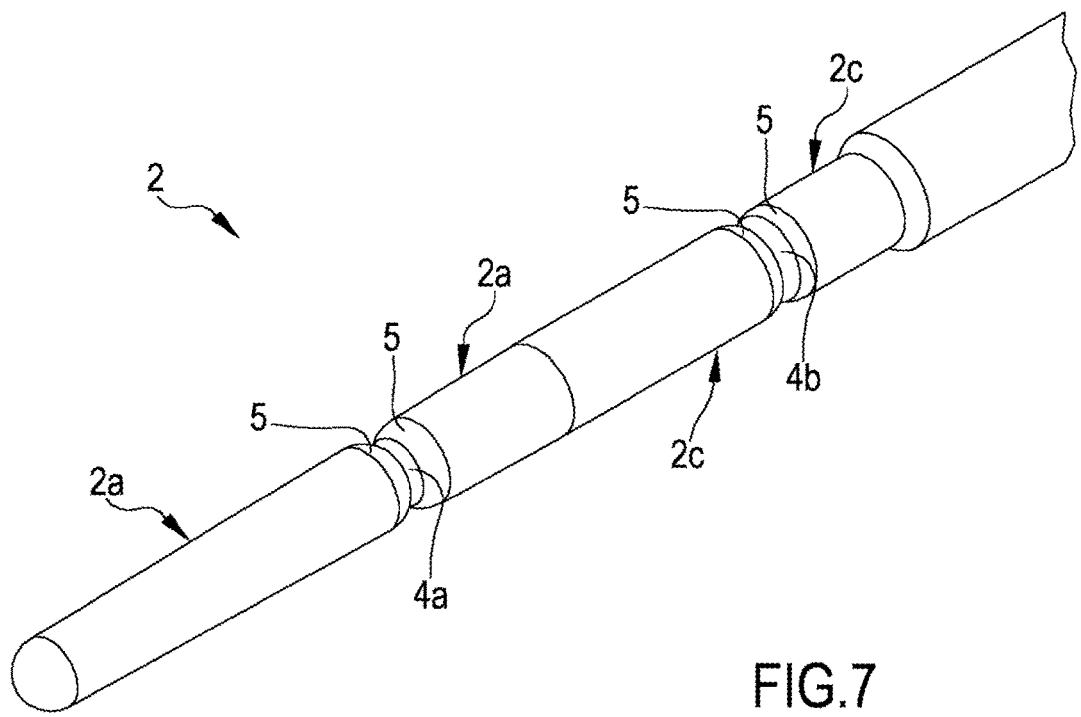

FLOCKED SWAB AND METHOD FOR COLLECTION AND TRANSFER OF SAMPLES OF BIOLOGICAL MATERIAL

CROSS-REFERENCE TO RELATED APPLICATIONS

This application is a U.S. National Phase Application under 35 U.S.C. § 371 and claims the benefit of priority to International Application No. PCT/IB2014/062201, filed on Jun. 13, 2014, which claims the benefit of priority to Italian Application No. MI2013A001088, filed on Jun. 28, 2013, the contents of which are hereby incorporated by reference.

The concepts herein relates to a flocked swab for collection and transfer of biological samples. The invention further relates to a process for realizing the flocked swab, a use of the flocked swab and a method for collection and transfer of samples of biological material by use of the flocked swab. The invention is for example applicable for collection and transfer of biological samples from crime scenes, for environmental collections of various types or for collections carried out directly from a human body and in particular human orifices, so as to enable conservation, transport and/or following analysis of the samples. The prior art includes the use of various types of collection and transfer devices for analytes, such as organic or biological substances, for example subsequently to be subjected to laboratory examinations of an analytic or diagnostic type. For example the prior art comprises swabs constituted by a rod, at a tip of which cotton fibre is wound or to which is associated a collection element, such as a sponge or the like, for defining a collecting portion aimed at absorbing internally thereof the sample to be collected. These devices tend to retain the sample internally of the collecting portion and to release only a small percentage of the sample for analytic purposes. Patent EP1608268 further discloses flocked swabs comprising an elongate support body and a plurality of flocked fibres at an end of the support body for defining a collecting portion for the analytes or biological samples. These flocked swabs enable release of a very high percentage of the absorbed biological samples. The above-described types of samples exhibit elongate rods which in general are realized in plastic materials that are more or less flexible according to the specific application, for example polystyrene or nylon. Sometimes the known swabs exhibit predetermined points of breakage, positioned at an intermediate portion of the elongate rod and specifically included so as to enable breakage of the rod at a precise and desired point with the aim of enabling conservation or transport of only the collecting portion, without the remaining gripping part, for example in order for the collecting portion to be inserted into test tubes or other containers for transport and analysis. The above-described known flocked swabs exhibit some drawbacks in the case of specific applications, such as for example the use thereof for collecting samples from crime scenes, where a part of the collection biological sample is to be analysed, while conserving a further part of the same sample with the aim of enabling a fully traceability of the sample and the carrying-out of any eventual re-analysis of the same sample at a later time. It is known that the collecting portion of the sample is generally treated with liquids or other substances with the aim of extracting the greatest possible quantity of biological sample therefrom, but this process prevents conserving a part of the sample for future use, as once the sample has been extracted from the collecting portion, the sample cannot be guaranteed to remain unaltered or substantially equivalent to what was originally collected. In an attempt to obviate this drawback, a manual process is for example known which consists in scraping a part of the fibres of the flocked portion of the device (or removing in a like way a part of the enveloping cotton fibre or the sponge defining the collecting portion), so as to subject only the scraped fibres separated from the rod to the sample extraction process, while conserving the rest of the swab and the flocked portion for a future use. This solution however exhibits some drawbacks, among which: a risk of contamination of the sample, the possibility of human error, the risk of having to repeat the process more than once in a case in which the part of fibre manually removed does not contain a sufficient quantity of biological sample, the laboriousness and cost connected to these manual operations. Further, it is an inefficient process that is expensive and which is further exposed to the risk of removing an excessive quantity of sample and not conserving a sufficient quantity for a future use.

In certain instances, the concepts herein obviate one or more of the problems encountered in the prior art.

In certain instances, the concepts herein are to disclose a method and a flocked swab for collection and transfer of biological samples which:

- facilitate and simplify obtaining of a sufficient quantity of sample to be analysed for immediate analysis and future uses; and/or
- guarantee a high degree of traceability and a correct conservation of the biological samples, even for long periods; and/or
- significantly reduce the risk of contamination of the collected samples; and/or
- increase the efficiency, safety and reliability of the treatment processes of the collected biological samples; and/or
- exhibit a high degree of flexibility and ease of use; and/or are simple and economical to actuate.

These aims and others besides, which will more fully emerge from the following description, are substantially attained by a method and a flocked swab according to what is set down in one or more of the appended claims, taken alone or in combination with one another or with any one of the aspects set down in the following. In a further aspect, taken alone or in combination with any further aspect or claim set down in the following, the invention further relates to a process for producing a flocked swab according to any one of the appended claims comprising at least a step of producing the support body of the flocked swab having at least a first portion and a step of applying, by flocking, a plurality of fibres on the first portion, so as to obtain at least a flocked collecting portion, the process further comprising a step of realizing, on the support body, at least a first weakening portion at the position of the flocked collecting portion by injection moulding of the support body or by material removal working of the support body following formation thereof. In a further aspect, taken alone or in combination with any further aspect expressed in the following or claim, the invention further relates to a use of a flocked swab, of the type claimed, for collection of biological samples from crime scenes, or environmental collections, or collections from a human body and/or a human orifice, in particular for collection of samples from the mouth, the pharynges, the nasal cavity, the eyes, the urethra, the vagina, the anus, the rectum or the skin, in which use a separation is made of the collecting portion containing a sample of biological material by breaking the support body at the first weakening portion so as to subdivide the flocked collecting portion at least into a first part and at least a second part. In the following, and by way of non-limiting example, a description is made of one or more preferred embodiments of the concepts herein, in which:

FIG. 6 is a further section of the support body of FIG. 4;

FIG. 6a is a larger-scale section view of a first weakening portion of the support body of FIG. 4;

FIG. 7 is a perspective view of a first portion of the support body of FIG. 4.

Figure 1:
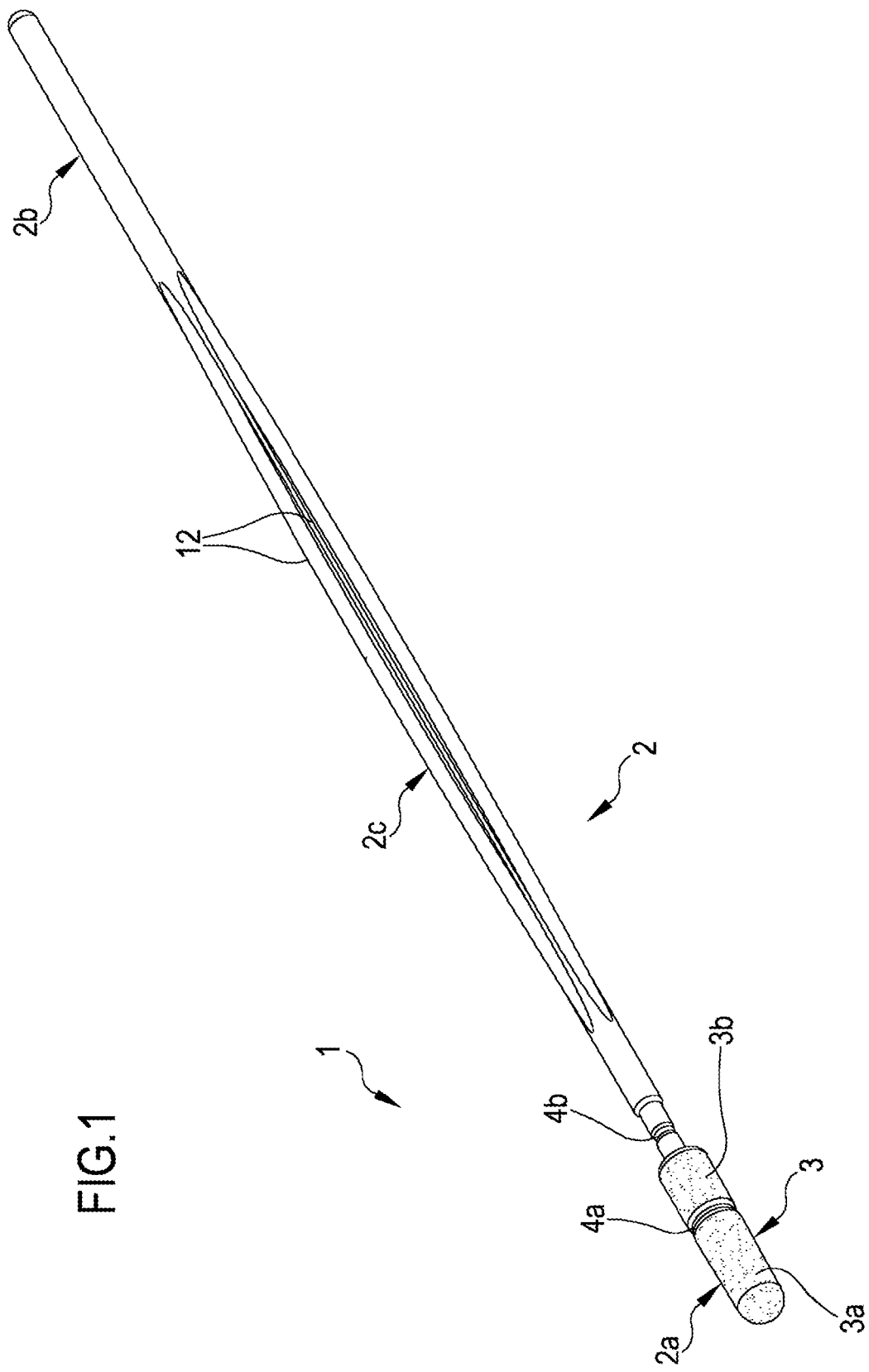
FIG. 1 is a perspective view of a flocked swab according to a first embodiment of the concepts herein.
Figure 2:
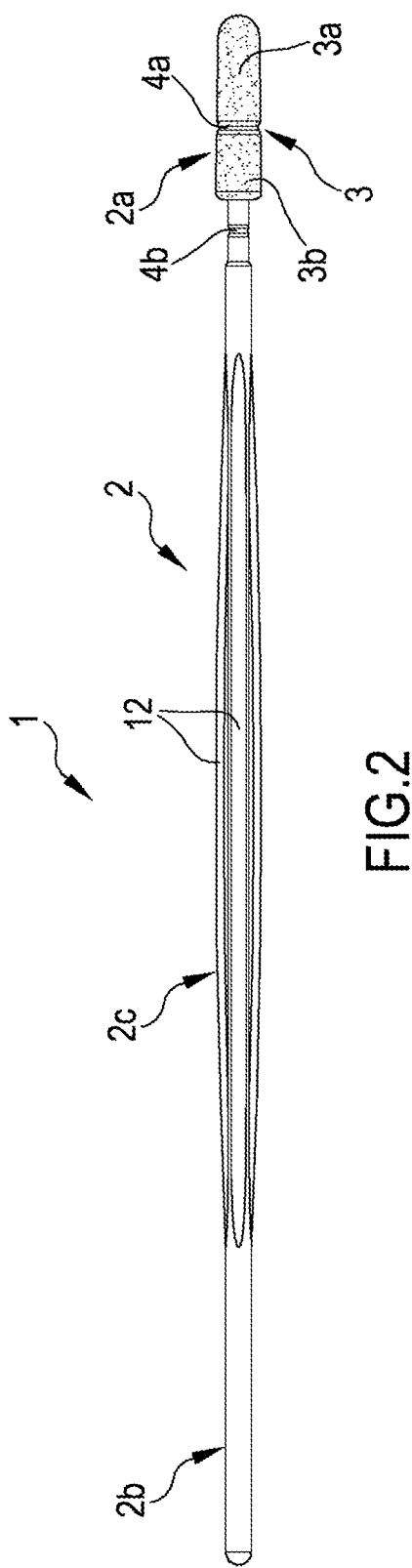
FIG. 2 is a lateral view of the flocked swab of FIG. 1.
Figure 3:
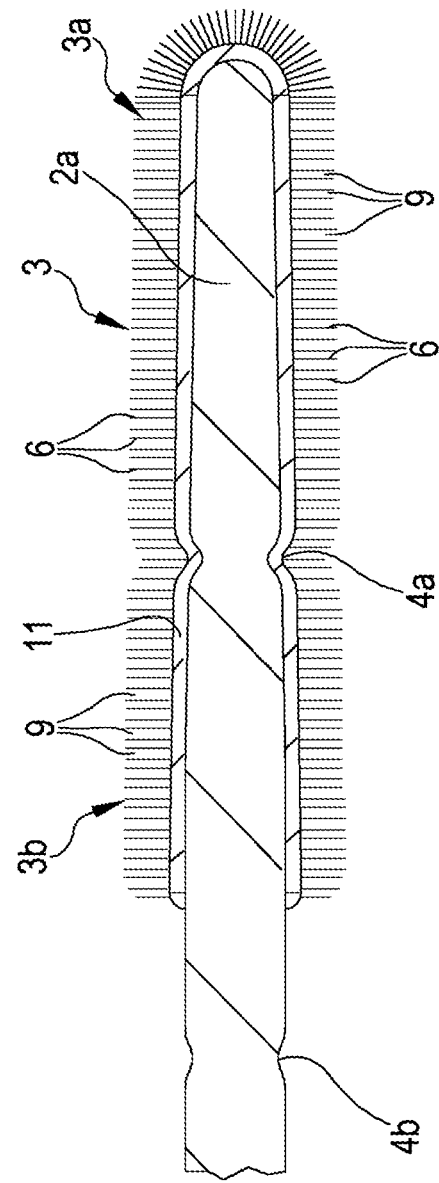
FIG. 3 is a schematic larger-scale view of a detail of the flocked swab of FIG. 1, relative to a flocked portion and a first weakening portion.
Figure 4:
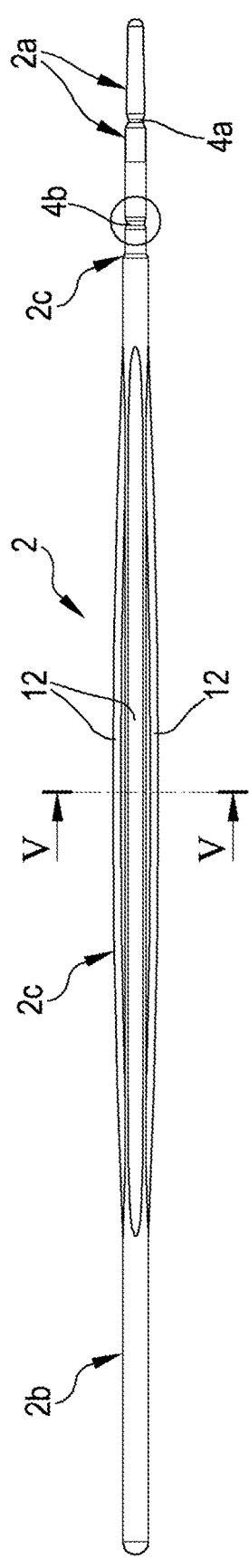
FIG. 4 is a lateral view of a support body of the flocked swab of FIG. 1.
Figure 6C:
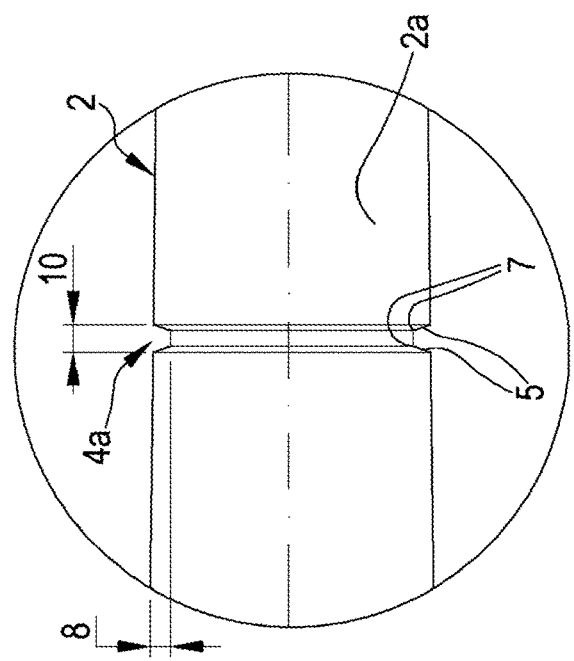
FIG. 6c is a larger-scale view of a variant of the first weakening portion of the support body of FIG. 4.
Figure 6B:
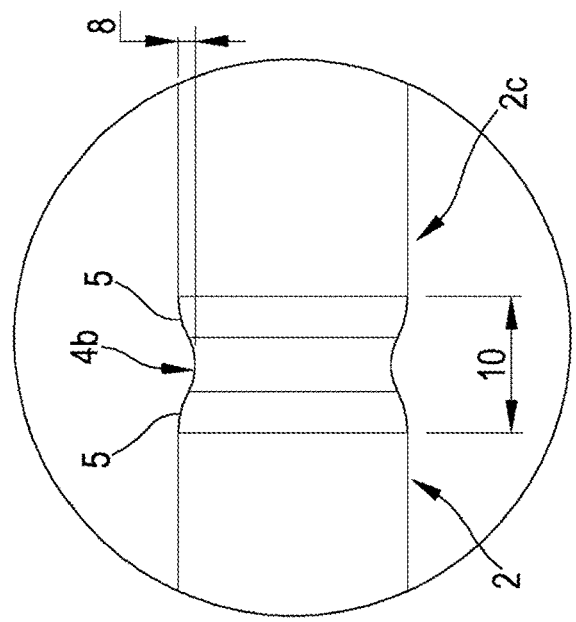
FIG. 6b is a larger-scale view of a second weakening portion of the support body of FIG. 4.
Figure 5:
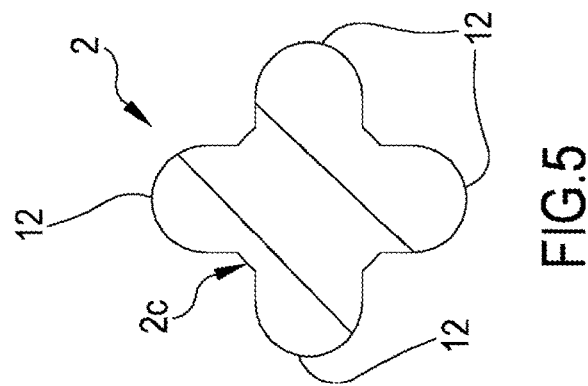
FIG. 5 is a section of the support body of FIG. 4.

In the following a description will be made of a flocked swab 1 for collection and transfer of biological samples according to one or more embodiments of the concepts herein. With reference to the accompanying figures, reference numeral 1 denotes in its entirety a flocked swab for collection and transfer of biological samples. The flocked swab 1 comprises a support body 2 which can be elongate and/or substantially rod-shaped. In detail the support body 2 can be a small rod as illustrated in the figures. The support body 2 can have any section, including a variable section along the longitudinal extension thereof. For example, the section can be circular, elliptical or can have any other shape suitable for the purpose. As can be seen in FIGS. 1, 2, 4 and 5, the support body 2 can be provided with a plurality of reinforcing ribs 12 having a longitudinal extension, at least at an intermediate portion 2c between a first end portion 2a and a gripping portion 2b. The support body 2 can be made of a plastic material, for example polypropylene and/or polyester and/or polyamide (PA66 or nylon 66). The support body can be made by injection moulding or by extrusion. The support body 2 can be foldable without breaking at least up to reaching a radius of curvature of 5 mm, or 4 mm or 3 mm or 2 mm or 1 mm. The support body 2 can be bendable without breaking for at least 10 cycles, or 20 cycles, or 50 cycles, or 100 cycles or 200 cycles of bending by 90° in opposite directions at an ambient temperature of about 25° C. The support body 2 is provided with a first portion 2a, for example an end portion defining a collecting portion 3 for the sample, a second portion, or gripping portion 2b, at which it can be manually grasped by an operator or can be connected to a further gripping element such as a test-tube cap or another suitable device, and a central third portion or intermediate portion 2c.

The collecting portion 3 for the sample can be conformed as a swab. The collecting portion 3 is of a flocked type, realized by flocking of a plurality of fibres 6 on the first portion 2a of the support body aimed at defining a flocked layer on the first portion 2a. The fibres 6 flocked on the first end can be made of a hydrophilic or non-hydrophilic material, but the collecting portion 3 is in any case hydrophilic by capillary effect because of the characteristics of the fibres 6 and the distribution thereof on the support body 2. In other terms, the collecting portion 3 can exhibit a continuous layer of fibres 6 made of a substantially adsorbent material, or preferably not adsorbent with respect to the sample, but in any case comprising a plurality of capillary interstices 9 among which a predetermined quantity of sample can be retained by imbibing, and from which the sample can be effectively released quantitatively at a suitable moment, for example by rubbing the collecting portion 3 on a suitable release surface or by dilution of the sample in a suitable diluent, or by centrifuging the sample in an appropriate device. The depositing of fibres by electrostatic flocking is carried out so as to produce, on the appropriate end of the flocked collecting swab 1 a substantially continuous and theoretically substantially homogeneous layer of a plurality of fibres 6 having a substantially ordered arrangement that is substantially perpendicular at each point of the first portion 2a of the support body 2 and each of which is substantially parallel to the adjacent fibres 6, at least according to a theoretical arrangement of the fibres. As already mentioned, the fibres 6 can be arranged on the support body 2 in a substantially ordered way and in such a way as to form a substantially continuous layer on the collecting portion 3 and are further advantageously arranged on the collecting portion 3 in such a way as to define a plurality of capillary interstices 9 aimed at adsorbing the sample by capillary effect. The flocked collecting portion 3 can be configured and dimensioned for collecting an appropriate amount of sample, or so as to collect a quantity of sample comprised for example between 5 and 1000 microlitres, or between 10 microlitres and 500 microlitres, or between 20 and 200 microlitres, or between 40 and 160 microlitres. The fibres 6 can exhibit a linear density comprised between 1 and 7 dtex or between 1.5 and 5 dtex, or between 1.7 and 3.3 dtex, and/or a length comprised between 0.2 mm and 3 mm or between 0.6 mm and 2 mm. The fibres 6 can be arranged by flocking on the collecting portion 3 of the support body 2 with a surface density for example comprised between 50 and 500 fibres per $mm^2$ or between 100 and 200 fibres per $mm^2$ of surface of the first portion 2a of the support body 2. The fibres can for example be glued on the support body 2 by an adhesive 11, for example a vinyl adhesive. In a further aspect of the concepts herein, the layer of fibres can define an absorbing capacity for example of at least 0.5 µl per $mm^2$, or at least 0.6 µl per $mm^2$, or at least 0.7 µl per $mm^2$, or at least 0.75 µl per $mm^2$ of surface of the support body 2. The fibres 6 can be made of a substantially non-hydrophilic or non-adsorbent material with respect to the sample, and/or of a substantially hydrophilic or adsorbent material with respect to the sample and/or of a material selected from among: polyamide (PA or nylon), rayon, polyester, carbon fibre, alginate, natural fibre, or a mixture of the materials. The fibres 6 are preferably made of nylon. The flocked swab 1 or the support body 2 can exhibit a longitudinal extension comprised between 50 mm and 200 mm or between 100 mm and 200 mm, or between 130 mm and 170 mm and/or a thickness or diameter in a perpendicular section to the central axis thereof comprised between 0.8 mm and 5 mm or between 1 mm and 4 mm or between 2 mm and 3 mm or between 2.3 mm and 2.7 mm. The collecting portion 3 can exhibit a longitudinal extension comprised between 3 mm and 40 mm or between 10 mm and 30 mm or between 15 mm and 20 mm and/or a diameter or thickness, including the fibres 6, comprised between 2 and 7 mm or between 3 and 6 mm or between 4.5 and 5.5 mm, or exhibits a diameter of the first portion, in a perpendicular section to the longitudinal extension thereof, without the fibres, comprised between 1 mm and 6 mm or between 2 mm and 5 mm or between 3.5 mm and 4.5 mm. The collecting portion 3 can exhibit any suitable shape for the type of sample to be collected or for the collection seating, for example rounded or with one or more sharp edges. The first portion 2a of the support body 2 is provided with at least a first weakening portion 4a, or break point, aimed at enabling and facilitating a selective breaking of the swab 1 at the first portion 2a and a separation of at least a first part 3a of the flocked collecting portion 3 from at least a second part 3b of the flocked collecting portion 3 and from the gripping portion 2b. The first weakening portion 4a is preferably positioned on the first portion 2a of the support body 2 in such a way as to define the first part 3a and the second part 3b of the flocked collecting portion 3 having substantially equal dimensions and/or a length that is substantially analogous in the prevalent development direction of the support body 2, in order to enable collection of substantially analogous quantities of the sample on the first part 3a and on the second part 3b of the flocked collecting portion 3. For example, the first weakening portion 4a can be positioned substantially intermediately on the first portion 2a of the support body 2. The layer of adhesive material 11 can also be present at the first weakening portion 4a. In a variant, the layer of adhesive material 11 can be absent at the first weakening portion 4a and the flocked layer can comprise a first part of flocked layer defining a first part of the collecting portion and a second part of flocked layer defining a second part of the collecting portion, the first and the second part of the collecting portion being distinct and separate at the first weakening portion 4a. The support body 2 can be further provided with a second weakening portion 4b, or break point, aimed at facilitating a selective breaking of the support body 2 in an intermediate position between the first end portion 2a or the collecting portion 3 and the second end portion of gripping portion 2b, in order to enable separation and facilitate, for example, insertion of the collecting portion 3 in a container for transport. The second weakening portion 4b can be realised on the support body 2 on the gripping portion 2b or on an intermediate portion 2c between the gripping portion 2b and the collecting portion 3 and/or in proximity of the collecting portion, as illustrated in the accompanying figures. The second weakening portion 4b can be realized at a distance from the end of the flocked portion and the flocked swab comprised between 10 mm and 100 mm, or between 15 and 90 mm or between 20 mm and 80 mm. The first portion 2a of the support body 2 can be further provided with at least a third weakening portion enabling a further selective breaking of the swab 1 at the first portion 2a and a separation of at least the second part 3b of the flocked collecting portion 3 from a third part 3c of the flocked portion 3 and from the gripping portion 2b. It is to be specified that the third weakening portion can be included also in the absence of the second weakening portion. The third weakening portion is not illustrated in the figures, but could for example be positioned in the same position as illustrated for the second weakening portion (in place thereof), in a case in which the flocked portion were to extend beyond that position, or it might be positioned in other positions in the flocked portion. In this case the second flocked portion could be absent or could be positioned displaced towards the gripping portion. The position of the first, second and/or third flocked portion could be different from what is illustrated and determined in accordance with the specific destination of use of the flocked swab. The first and the third weakening portion can be arranged in such a way as to enable a selective breaking of the swab 1 in a first, second and third part of dimensions and/or length that are substantially identical or analogous to one another. The first, second and/or third weakening portion 4a, 4b can be configured for enabling the selective breaking in the presence of a bending of the support body 2 at least on reaching a radius of curvature of 10 mm or 6 mm or 4 mm or 2 mm or 1 mm. The first, second and/or third weakening portion 4a, 4b can be configured for enabling the selective breaking in the presence of at least one, or one only, complete bending of the support body on itself with an angle of less than 90° or 60° or 40° or 20° or 10° or 5°. The first, second and/or third weakening portion 4a, 4b, can be configured such that the two lateral walls 5 defined by the weakening portion enter into reciprocal contact, determining a lever effect aimed at causing the selective breaking, following a folding of the body in the presence of at least one, or one only, complete folding of the support body on itself with an angle of less than 90° or 60° or 40° or 20° or 10° or 5°. The first, second and/or third weakening portion 4a, 4b can be configured so as not to enable the selective breaking in the presence of a folding of the support body of a radius of curvature of greater than 1 mm or 2 mm or 4 mm or 6 mm or 10 mm. The first, second and/or third weakening portion 4a, 4b can be configured so as not to enable the selective breaking in the presence of at least one, or one only, complete folding of the support body on itself with an angle of greater than 2° or 5° or 10° or 20° or 30°. The first, second and/or third weakening portion 4a, 4b can be constituted by a reduction in circumferential or perimeter thickness of the support body. The first, second and/or third weakening portion 4a, 4b can include a reduction in diameter of the support body 2 in a perpendicular section to the longitudinal extension of at least 0.1 mm or at least 0.2 mm or at least 0.4 mm or at least 0.8 mm, or at least 1 mm. The first, second and/or third weakening portion 4a, 4b can include a reduction in diameter of the support body in perpendicular section to the longitudinal extension of at least 5% or at least 10% or at least 20% or at least 30% or at least 40% or at least 50%. The first, second and/or third weakening portion can exhibit a substantially rounded conformation having a radius of curvature of less than 2 mm or 1 mm or 0.5 mm. The first, second and/or third weakening portion can exhibit a concave conformation having at least a sharp edge 7, or at least two sharp edges 7, for facilitating the breakage. To facilitate the breakage, the depth 8 of the weakening portion 4a, 4b is equal to at least 0.6 times the width 10 thereof on the surface of the support body, or at least 0.8 times the width, or it is at least equal to the width thereof, or it is equal to at least 1.2 times the width thereof, or at least 1.5 times the width thereof. The first and/or the second and/or the third weakening portion 4a, 4b can be realized by injection moulding of the support body or, in a variant, can be realized or completed by material removal working of the support body following formation thereof. The support body 2 can be provided with a plurality of reinforcing ribs 12 having a longitudinal extension, at least at an intermediate portion 2c between the first portion 2a and the gripping portion 2b. The flocked collecting swab 1 can be realised in a plurality of different support bodies 2, each provided with a collecting portion 3 having a different conformation or shape and specifically configured for collecting a sample in a specific seating, or for collecting a specific quantity of sample. The flocked collecting swab 1 can further comprise a container for transport of the sample having an internal containing seating and an access opening. The container, not illustrated as of known type, can be a test tube for transport of samples of biological material or material of biological origin. The flocked swab 1 can further comprise a closing cap removably mountable on the access opening for selectively closing the container. The container and/or the closing cap can be made of a plastic material, for example polystyrol or polystyrene or polypropylene and/or of a suitable material for use with the specific sample to be collected, or in generally suitable for use with biological materials or materials of biological origin. The container and/or the closing cap and/or the support body 2 can be sterilised. The flocked collecting swab 1 can further comprise a sealed pack (not illustrated in the figures as of known type) in which the support body 2 and/or the container and the closing cap can be housed before use for collecting a sample. The support body 2, the pack, the container and the cap can be sterile. The concepts herein further relate to a use of a flocked swab described for the collection of biological samples from crime scenes, or when taking environmental samples, or for collections from a human body and/or a human orifice, in particular for collection of samples from the mouth, the pharynges, the nasal cavity, the eyes, the urethra, the vagina, the anus, the rectum or the skin, in which use a separation is made of the collecting portion containing a sample of biological material by breaking the support body at the first weakening portion so as to subdivide the flocked collecting portion at least in a first part and at least a second part. The concepts herein further relate to a process for realizing a flocked swab 1 of the above-described type. The process can comprise for example following steps: realizing the support body 2, for example by injection moulding or by extrusion; applying an appropriate glue 11 to the first portion 2a of the body 2; applying the fibres 6 to the first portion 2a by flocking in an electromagnetic field; drying the glue 11 in a suitable oven of conventional type so as to polymerise at least partially the glue 11. In accordance with an aspect of the concepts herein, the process further comprises a step of realizing on the support body at least a first weakening portion at the flocked collecting portion by injection moulding of the support body or by material removal working of the support body following the formation thereof. The concepts herein further relate to a method for collection and transfer of material by a flocked swab 1 of the above-described type. The method further comprises a step of putting at least the first part 3a and the second part 3b of the flocked collecting portion 3 of the swab in contact with a biological sample in such a way as and for a time aimed at collecting at least a first quantity of the biological sample on the first part 3a and at least a second quantity of the biological sample on the second part 3b of the flocked collecting portion 3 of the collecting swab 1. The method further comprises a step of separating the first part 3a of the flocked collecting portion 3 containing the first quantity of biological sample at least from the second part 3b of the flocked collecting portion 3 containing the second quantity of biological sample of the collecting swab and from the gripping portion 2b. The method further comprises a step of extracting at least a part of the first quantity of the biological sample from the first part 3a of the flocked collecting portion 3 in order to enable carrying out analytical operations on the biological sample at a first time and conserving the second quantity of biological sample on the second part 3b of the flocked collecting portion 3 for a future use following the first time, or vice versa extracting at least a part of the second quantity of biological sample from the second part 3a of the flocked collecting portion 3 in order to enable carrying out analytical operations on the biological sample at a first time and conserving the first quantity of biological sample on the first part 3b of the flocked collecting portion 3 for a future use following the first time. The method can further comprise a step of conserving the sample on the collecting portion 3, or only on the first or only on the second part of the collecting portion 3, for a predetermined amount of time. The method can further comprise a step of dehydrating or drying at least the collecting portion 3, either only the first or only the second part of the collecting portion 3 provided with the collected sample. The drying step can be carried out, for example, by forced-ventilation oven-drying or by another methodology of known type and suitable for treatment of the sample, for example by use of silicon gel. The method can further comprise a step of rehydrating the sample on the collecting portion 3, either only of the first or only on the second part of the collecting portion 3, for example by at least a hydrating solution, in order to obtain a predetermined quantity of rehydrated sample on the collecting portion 3. The method can further comprise steps of inserting the collecting portion 3, either only the first or only the second part of the collecting portion 3, including the sample, in a container such as for example a test tube, closing the container by a closing cap or lid and transferring the container comprising the collecting portion 3 and/or the step of predisposing in the container a predetermined quantity of a substance aimed at liquefying and/or conserving the sample and/or the step of agitating, shaking or rotating the container comprising the collecting portion 3, either only the first or only the second part of the collecting portion 3, with the sample at a predetermined velocity and aimed at liquefying the sample. The concepts herein enable obtaining one or more of the following advantages. Primarily, the concepts herein enable realizing a process, a flocked swab realized according to the process, and a method for using the flocked swab that obviate the problems encountered in the prior art. In particular, the concepts herein further enable realizing flocked swabs which simplify the obtaining of a sufficient quantity of sample to be analysed for immediate analyses and for future uses. The concepts herein further enable guaranteeing a high traceability and a correct conservation of the biological samples even for long periods. The concepts herein further enable significant reduction of the risk of contamination of the collected samples. The concepts herein further enable increasing the efficiency, safety and reliability of the treatment processes of the collected biological samples. The swabs of the concepts herein further exhibit a high degree of ease of use as well as good levels of reliability and safety of use. Lastly, the concepts herein are simple and economic to manufacture.

The invention claimed is:

1. A flocked swab for collection and transfer of samples of biological material, wherein the flocked swab comprises:
   a support body having an elongated conformation and having a first end portion and a gripping portion, and
   a flocked layer defined by a plurality of fibres attached and arranged on the first end portion of the support body by flocking, so as to realize a flocked collecting portion configured for absorbing a quantity of a sample of biological material, said flocked layer comprising, in correspondence of said first end portion, a first part and a second part, said first end portion comprising a first part and a second part;

wherein:
   the first end portion of the support body comprises a first weakening portion arranged at an intermediate point between the first part of the flocked layer and the second part of the flocked layer, and being configured for enabling and facilitating a first selective breakage of the support body of the flocked swab in correspondence of the first end portion and a first separation of the first part of the flocked collecting portion and of the first end portion from the second part of the flocked collecting portion, the second part of the first end portion and from the gripping portion; and the support body comprises a second weakening portion, arranged in an intermediate position between the first end portion or the collecting portion and the gripping portion, the second weakening portion being configured for enabling a selective breakage of the support body and a second separation of the flocked collecting portion from a part of the gripping portion.

2. The flocked swab of claim 1, wherein the second weakening portion is realized at a distance from the end of the flocked collecting portion and the flocked swab comprised between 15 mm and 90 mm.

3. The flocked swab of claim 2, wherein the first end portion of the support body comprises a third weakening portion configured for enabling a third selective breaking of the flocked swab at the first end portion and a third separation of the second part of the flocked collecting portion from a third part of the flocked collecting portion and the gripping portion.

4. The flocked swab of claim 1, wherein the second weakening portion is configured for enabling the selective breaking in a presence of a manual folding of the support body or a folding of the support body on reaching a radius of curvature of 4 mm or to enable the selective breakage in the presence of one, or one only, complete folding of the support body on itself with an angle of less than 60° or is conformed in such a way that two lateral walls defined by the second weakening portion enter into contact with one another, determining a lever effect configured for causing the selective breaking, following a folding of the support body in the presence of one, or one only, complete folding of the support body on itself with an angle of less than 60° or wherein the second weakening portion is configured so as not to enable the second selective breaking in the presence of a folding of the support body with a radius of curvature of greater than 4 mm.

5. The flocked swab of claim 3, wherein the third weakening portion is configured for enabling the selective breaking in a presence of a manual folding of the support body or a folding of the support body on reaching a radius of curvature of 4 mm or to enable the third selective breaking in the presence of one, or one only, complete folding of the support body on itself with an angle of less than 60° or is conformed in such a way that two lateral walls defined by the third weakening portion enter into contact with one another, determining a lever effect configured for causing the third selective breaking, following a folding of the support body in the presence of one, or one only, complete folding of the support body on itself with an angle of less than 60° or wherein the third weakening portion is configured so as not to enable the selective breaking in the presence of a folding of the support body with a radius of curvature of greater than 4 mm.

6. The flocked swab of claim 3, wherein the third weakening portion comprises a circumferential or perimetral reduction in thickness of the support body or exhibit a reduction in diameter or thickness of the support body in a perpendicular section to a longitudinal extension thereof of at least 0.1 mm or a reduction in diameter or thickness of the support body in perpendicular section to the longitudinal extension thereof of at least 5% or exhibits a rounded conformation having a radius of curvature of less than 2 mm or a concave conformation and having a sharp edge, or two sharp edges, so as to facilitate breakage or wherein the depth of the weakening portion is equal to at least 0.6 times the width thereof on the surface of the support body.

7. The flocked swab of claim 1, further comprising a layer of adhesive material or vinyl adhesive arranged on the first end portion so as to enable adhesion of the plurality of fibres on the first end portion and wherein the layer of adhesive material is present also on the first weakening portion, or wherein the layer of adhesive material is absent at the first weakening portion and wherein the flocked layer comprises a first part of flocked layer defining a first part of the collecting portion and a second part of flocked layer defining a second part of the flocked collecting portion, the first and the second part of the collecting portion being distinct and separate from the first weakening portion.

8. A flocked swab for collection and transfer of samples of biological material, wherein the flocked swab comprises at least:
   a support body having an elongate conformation and having at least a first end portion and at least a gripping portion, and
   at least a flocked layer defined by a plurality of fibres attached and arranged on the first end portion of the support body by flocking, so as to realize a flocked collecting portion configured for absorbing a quantity of a sample of biological material, wherein the first end portion of the support body is provided with at least a first weakening portion configured for enabling and facilitating a first selective breakage of the first end portion of the support body and a first separation of at least a first part of the flocked collecting portion:
   from at least a second part of the flocked collecting portion, and
   from the gripping portion of the support body;
the flocked swab further comprising a layer of adhesive material or vinyl adhesive arranged on the first end portion of the support body so as to enable adhesion of the plurality of fibres on the first end portion of the support body and wherein the layer of adhesive material or vinyl adhesive is present also on the first weakening portion.

9. The flocked swab of claim 8, wherein the first weakening portion exhibits a reduction in diameter or thickness of the support body in a perpendicular section to a longitudinal extension thereof of at least 0.2 mm.

10. The flocked swab of claim 8, wherein the first weakening portion is configured for enabling the selective breaking in the presence of a manual folding of the support body or a folding of the support body on reaching a radius of curvature of or to enable the first selective breakage in a presence of one, or one only, complete folding of the support body on itself with an angle of less than 60° or is conformed in such a way that two lateral walls defined by the first weakening portion enter into contact with one another, determining a lever effect configured for causing the selective breaking, following a folding of the support body in the presence of one, or one only, complete folding of the support body on itself with an angle of less than 60° or wherein the first weakening portion is configured so as not to enable the selective breaking in the presence of a folding of the support body with a radius of curvature of greater than 1 mm.

11. The flocked swab of claim 8, wherein the first weakening portion comprises a circumferential or perimetral reduction in thickness of the support body or exhibits a reduction in diameter or thickness of the support body in a perpendicular section to a longitudinal extension thereof of at least 0.1 mm or a reduction in diameter or thickness of the support body in perpendicular section to the longitudinal extension thereof of at least 5% or exhibits a rounded conformation having a radius of curvature of less than 2 mm or a concave conformation and having a sharp edge, or two sharp edges, so as to facilitate breakage or wherein the depth of the first weakening portion is equal to at least 0.6 times a width thereof on a surface of the support body.

12. The flocked swab of claim 8, wherein the support body is realized by injection moulding or extrusion or wherein the support body is provided with a plurality of reinforcing ribs having a longitudinal extension, at an intermediate portion between the first end portion and the gripping portion or wherein the support body is a rod made of polypropylene or of polystyrene or polyamide (PA or nylon), in particular polyamide 66 (PA66 or nylon 66).

13. The flocked swab of claim 8, wherein the support body exhibits a length, in a longitudinal extension thereof, comprised between 100 mm and 200 mm or exhibits, at the gripping portion, a thickness or diameter in perpendicular section to the longitudinal extension thereof comprised between 0.8 mm and 5 mm or wherein the support body exhibits a length of the flocked collecting portion comprised between 10 mm and 30 mm or exhibits a diameter of the flocked collecting portion, in a perpendicular section to the longitudinal extension thereof, comprising the length of the plurality of fibres, comprised between 3 mm and 6 mm or exhibits a diameter of the first end portion, in perpendicular section to the longitudinal extension, without the plurality of fibres, comprised between 2 mm and 5 mm.

14. The flocked swab of claim 8, wherein the flocked collecting portion is configured for collecting a quantity of sample comprised between 10 microlitres and 500 microlitres or wherein the plurality of fibres are arranged on the first end portion of the support body in an ordered way and such as to form a continuous layer on the flocked collecting portion or are arranged on the flocked collecting portion in such a way as to define a plurality of capillary interstices configured for absorbing, by capillary action, the sample or wherein the plurality of fibres exhibit a linear density comprised between 1.5 and 5 dtex or a length comprised between 0.2 mm and 3 mm or are made of a non-hydrophilic or non-adsorbent material with respect to the sample, or of a hydrophilic or adsorbent material with respect to the quantity of sample or of polyamide (PA or nylon) or of a material selected from among: rayon, polyester, carbon fibre, alginate, natural fibre, or a mixture of said materials or wherein the collecting portion exhibits a surface density of the fibres on the flocked collecting portion comprised between 50 and 500 fibres per mm$^2$.

15. The flocked swab of claim 8, wherein the first weakening portion exhibits a reduction in diameter or thickness of the support body in a perpendicular section to a longitudinal extension thereof of at least 0.1 mm.

16. The flocked swab of claim 8, wherein the first weakening portion exhibits a reduction in diameter or thickness of the support body in perpendicular section to a longitudinal extension thereof of at least 5%.

17. The flocked swab of claim 8, wherein the first weakening portion exhibits a rounded conformation having a radius of curvature of less than 2 mm.

18. The flocked swab of claim 8, wherein the first weakening portion exhibits a concave conformation having a sharp edge, or two sharp edges, so as to facilitate breakage.

19. The flocked swab of claim 8, wherein a depth of the first weakening portion is equal to at least 0.6 times a width thereof on a surface of the support body.

20. The flocked swab of claim 8, wherein the first weakening portion exhibits a reduction in diameter or thickness of the support body in perpendicular section to a longitudinal extension thereof of at least 10%.

21. The flocked swab of claim 8, wherein the first weakening portion exhibits a substantially rounded conformation having a radius of curvature of less than 1 mm.

22. The flocked swab of claim 8, wherein the first weakening portion exhibits a concave conformation and has a sharp edge, or two sharp edges, so as to facilitate breakage.

23. The flocked swab of claim 8, wherein a depth of the first weakening portion is equal to at least 0.8 times a width thereof on a surface of the support body.

24. The flocked swab of claim 8, wherein the first weakening portion is realized by injection moulding of the support body.

25. The flocked swab of claim 8, wherein the first weakening portion is realised by material removal working of the support body following a formation thereof.

26. A method for collecting and transferring samples of biological material by a flocked swab according to claim 8, the method comprising:
   putting in contact the first part and the second part of the flocked collecting portion of the flocked swab with a biological sample in such a way that and for a time required for collecting a first quantity of the biological sample on the first part and a second quantity of the biological sample on the second part of flocked collecting portion of the flocked swab;
   separating the first part of the flocked collecting portion containing the first quantity of biological sample from the second part of the flocked collecting portion containing the second quantity of biological sample of the flocked swab and the gripping portion; and
   extracting a part of the first quantity of the biological sample from the first part of the flocked collecting portion in order to enable performing analysis on the biological sample at a first time moment and conserving the second quantity of the biological sample on the second part of the flocked collecting portion for a future use following the first time moment, or vice versa extract a part of the second quantity of the biological sample from the second part of the flocked collecting portion in order to enable performing analytical operations on the biological sample at a first time moment and conserve the first quantity of the biological sample on the first part of the flocked collecting portion for a future use after the first time moment.

* * * * *

UNITED STATES PATENT AND TRADEMARK OFFICE
CERTIFICATE OF CORRECTION

PATENT NO. : 10,517,575 B2
APPLICATION NO. : 14/901588
DATED : December 31, 2019
INVENTOR(S) : Daniele Triva Page 1 of 1

It is certified that error appears in the above-identified patent and that said Letters Patent is hereby corrected as shown below:

On the Title Page

Column 1 item (30) (Foreign Application Priority Data), Line 1, delete "MI13A1088" and insert -- MI2013A001088 --.

Signed and Sealed this
Seventh Day of April, 2020

Andrei Iancu
*Director of the United States Patent and Trademark Office*